United States Patent [19]

Chen et al.

[11] Patent Number: 5,780,563
[45] Date of Patent: Jul. 14, 1998

[54] SUPPORTED LEWIS ACID CATALYSTS DERIVED FROM SUPERACIDS USEFUL FOR HYDROCARBON CONVERSION REACTIONS

[75] Inventors: Frank Joung-yei Chen, Edison, N.J.; Alain Guyot, Lyons; Thierry Hamaide, Vienne, both of France; Christophe Le Deore, Edison, N.J.

[73] Assignee: Exxon Chemical Patents Inc., Linden, N.J.

[21] Appl. No.: 788,315

[22] Filed: Jan. 24, 1997

Related U.S. Application Data

[62] Division of Ser. No. 680,073, Jul. 15, 1996, Pat. No. 5,607,890, which is a continuation of Ser. No. 220,769, Mar. 31, 1994, abandoned.

[51] Int. Cl.⁶ .................................................. C08F 4/18
[52] U.S. Cl. ........................ 526/130; 502/44; 502/202; 502/408; 526/120; 526/126; 526/123.1; 526/131; 526/137; 526/138; 526/156; 526/226; 526/234
[58] Field of Search .................. 526/130, 126, 526/234, 137, 138; 502/202, 44, 408

[56] References Cited

U.S. PATENT DOCUMENTS

| | | | |
|---|---|---|---|
| 3,248,343 | 4/1966 | Kelly | 502/231 |
| 3,539,633 | 11/1970 | Piasek et al. | |
| 3,629,150 | 12/1971 | Addy | 502/231 |
| 3,649,229 | 3/1972 | Otto | |
| 4,116,880 | 9/1978 | Olah | 252/429 R |
| 4,719,190 | 1/1988 | Drago et al. | 502/64 |
| 4,798,667 | 1/1989 | Drago et al. | 208/117 |
| 4,857,612 | 8/1989 | Bacskai | 526/125 |
| 4,929,800 | 5/1990 | Drago et al. | 585/744 |
| 5,245,103 | 9/1993 | Wu | 585/743 |

FOREIGN PATENT DOCUMENTS

| | | |
|---|---|---|
| 0539277 | 4/1993 | European Pat. Off. |
| 2691380 | 11/1993 | France |

OTHER PUBLICATIONS

Encyclopedia of Chemical Technology, Third Edition, vol. 11, "Fluorine Compounds, Organic to *Gold and Gold Compounds*", Subsection: *Friedel–Crafts Reactions*, pp. 295–296 *(1980) by John Wiley & Sons, Inc..*

G.A. Olah et al., Science, vol. 206, No. 4414, pp. 13–20, Oct. 5, 1979.

Encyclopedia of Chemical Technology, Third Edition, vol. 10, "Ferroelectrics to Fluorine *Compounds, Organic*", Subsection: *Fluorine Compounds, Inorganic, pp. 733–753 (1980) by John Wiley & Sons, Inc..*

E.S. Gould, "Inorganic Reactions and Structure", (1955), 88–89, Holt (New York).

"Solid Superacid Catalyst", Chemtech, Nov. 1993, Makoto Misono, Toshio Okuhara, pp. 23–29.

*Primary Examiner*—Fred Zitomer
*Attorney, Agent, or Firm*—Harvey L. Cohen

[57] ABSTRACT

A supported Lewis acid catalyst system for catalyzing hydrocarbon conversion reactions including cationic polymerization, alkylation, isomerization and cracking reactions is disclosed, wherein the catalyst system comprises an inorganic oxide support having immobilized thereon a least one strong Lewis acid comprising at least one metal salt of a strong Bronsted acid wherein the metal is selected from the group consisting of aluminum, boron gallium, antimony, tantalum, niobium, yttrium, cobalt, nickel, iron, tin, zinc, magnesium barium strontium, calcium, tungsten, molybdenum and the metals of the lanthanide series and wherein the strong Bronsted acid is selected from the group consisting of mineral and organic acids stronger than 100% sulfuric acid.

8 Claims, No Drawings

SUPPORTED LEWIS ACID CATALYSTS DERIVED FROM SUPERACIDS USEFUL FOR HYDROCARBON CONVERSION REACTIONS

Division of Ser. No. 680,073, Jul. 15, 1996, U.S. Pat. No. 5,607,890, which is a continuation of Ser. No. 220,769, Mar. 31, 1994, abandoned.

TECHNICAL FIELD

This invention relates to supported Lewis acid catalyst systems, to processes for preparing the catalyst systems, and to various hydrocarbon conversion reactions which are performed in the presence of such catalyst systems. More particularly, the invention relates to effective catalyst systems for cationic polymerization, alkylation, isomerization and cracking reactions comprising at least one Lewis acid immobilized on an inorganic substrate containing surface hydroxyl groups, wherein the at least one Lewis acid is a relatively strong Lewis acid derived from a mineral acid or an organic acid. The immobilized catalysts are active to induce the carbocationic polymerization of monoolefins in polar or non-polar reaction media, are insoluble in the polymerization reaction medium, and result in minimal catalyst consumption and polymer contamination.

BACKGROUND OF THE INVENTION

Lewis acids are among the most powerful initiators for hydrocarbon conversion reactions. Such catalysts have been used in liquid, gaseous and solid form, and have been supported or immobilized on various polymeric and inorganic substrates, including, for example, silica gel, alumina, graphite and various clays.

Both supported and unsupported Lewis acid catalysts have been used with varying degrees of success for initiating alkylation reactions, in the carbocationic polymerization of olefins, such as isobutene, and in hydrocarbon isomerization and cracking reactions. For example, in copending patent application U.S. Ser. No. 064,688, filed May 20, 1993, incorporated herein by reference, there are described solid state insoluble salt catalysts based on at least one solid state insoluble salt selected from the group consisting of the salts of a strong acid and a Group IIIA–VIA transition metal selected from the group consisting of yttrium, lanthanum, zirconium, hafnium, niobium, tantalum, molybdenum and tungsten. Solid state catalysts have been studied for use in the carbocationic polymerization of olefins; a number of these catalysts have been based on the use of a catalyst on a polymeric substrate.

U.S. Pat. No. 4,116,880 discloses a catalyst comprising a fluorinated graphite support having certain Lewis Acids bonded thereto. The Lewis Acids are selected from the halides of the metals of Group IIA, IIIA, IVB, VA, VB or VIB. This patent also discusses superacid catalysts which are supported, for example, on fluorinated alumina, on inert polyfluorinated polymer supports such as polytetrafluoroethylene (Teflon), or on fluorinated polycarbon (coke). The catalysts based on fluorinated alumina are said to show limited adherence of the catalyst to the surface.

U.S. Pat. Nos. 4,719,190, 4,798,667 and 4,929,800 disclose hydrocarbon conversion catalysts prepared by reacting a solid adsorbent containing surface hydroxyl groups with certain Lewis acid catalysts in halogenated solvent. The Lewis acids disclosed as useful in the reference are limited to aluminum and antimony halides and the resulting reaction product is the final catalyst of the invention.

However, in spite of the advances made in the field of hydrocarbon conversion catalysis relating to Lewis acids, there continues to be interest in developing highly efficient catalyst systems which can be recycled or reused in such processes, e.g., in cationic polymerization, alkylation, isomerization and cracking processes. The present invention was developed pursuant to this interest.

SUMMARY OF THE INVENTION

In accordance with one aspect of the present invention, there is provided an immobilized Lewis acid catalyst system which comprises a metal selected from the group consisting of aluminum, boron gallium, antimony, tantalum, niobium, yttrium, cobalt, nickel, iron, tin, zinc, magnesium barium strontium, calcium, tungsten, molybdenum and the metals of the lanthanide series, which metal is in the form of a salt of a strong Bronsted acid selected from the group consisting of acids equal to or stronger than 100% sulfuric acid, including mineral and organic acids; in particular the acid has a Hammett acidity value of at least minus 12 or lower, preferably minus 13 or lower (such acids being characterized as "superacids" with an acidity equal to or stronger than 100% sulfuric acid). Furthermore, the acids useful in the present invention are those acids that give up a proton, characterized as "Lowry-Brønsted" (hereinafter Bronsted acids) rather than Lewis acids or mixed Bronsted/Lewis acids. A super acid of the latter type is the mixture HF—SbF$_5$ (1:1) whereas acids of the former type include FSO$_3$H and CF$_3$SO$_3$H. Such a catalyst system is active for various hydrocarbon conversion reactions, including, in particular, carbocationic olefin polymerization and alkylation reactions. According to this aspect, the immobilized catalyst system is in the form of a particulate inorganic substrate on which there is supported or immobilized the Lewis acid. The particulate inorganic substrate which is to be used as the catalyst support may comprise any conventional inorganic substrate having surface hydroxyl groups, i.e., —OH groups. Such substrates include, for example, powders comprised of or including silica, alumina, magnesia, titania, zeolites, silica-alumina, silica-titania, silica-magnesia or the like.

In another aspect, an immobilized Lewis acid catalyst system may be prepared by reacting an inorganic, silicon-containing substrate having surface silanol groups, i.e., Si—OH groups, with at least one Lewis acid selected from the group X$_n$MR$_m$, wherein M is a metal selected from the group consisting of aluminum, boron gallium, antimony, tantalum, niobium, yttrium, cobalt, nickel, iron, tin, zinc, magnesium barium strontium, calcium, tungsten, molybdenum and the metals of the lanthanide series, R is a monovalent hydrocarbon radical, preferably C$_1$–C$_{12}$ alkyl or aryl, and X is a halide selected from the group consisting of bromine, chlorine and fluorine and n and m are integers sufficient to satisfy the valence requirements of M; such that a portion of the silanol groups on the substrate are converted to Si—O—MX$_n$R$_{m-1}$ groups, and are additionally contacted with at least one strong Bronsted acid, SH, wherein the strong Bronsted acid is as described above, such that the Si—O—MX$_n$R$_{m-1}$ groups are substantially converted to Si—O—MS$_{n+m-1}$.

Another aspect of the present invention provides a process for using the above immobilized Lewis acid catalyst system for polymerizing a variety of monomers into homopolymers and copolymers, e.g., polyalkenes, by contacting the monomers with the immobilized Lewis acid catalyst system of this invention under carbocationic polymerization conditions. The monomers which may be used according to this aspect of the invention include those having unsaturation which are conventionally polymerizable using carbocationic Lewis acid catalyst polymerization techniques, such as, for example, olefins characterized by the presence in their structure of the group >C=CH$_2$. To effect cationic polymerization in a preferred process of the present invention, at least one inlet stream comprising monomer feed to be polymerized is fed to a reactor having at least one discharge stream. The monomer stream is polymerized in the reactor in the presence of the above-described immobilized Lewis acid catalyst system. The resulting polymerized polymer is removed from the reactor along with the unreacted monomers in the discharge stream while the immobilized catalyst system is retained in the reactor.

Yet another aspect of the invention is the preparation of an olefin polymer product which is characterized by having a high degree of reactive vinylidene unsaturation. In this aspect, it has been found, for example, that about 40% of the polymer chains of polyisobutylene which has been prepared by cationic polymerization in the presence of the above-described Lewis acid catalyst systems exhibit terminal or non-terminal vinylidene unsaturation. In contradistinction, typically less than about 20% of the polymer chains of polyisobutylene prepared using a conventional non-supported strong Lewis acid catalyst, e.g., ethyl aluminum dichloride, will contain terminal or non-terminal vinylidene unsaturation.

In still other aspects, the catalyst systems of this invention may be used in hydrocarbon conversion processes such as isomerization, cracking and alkylation. As is known in the art, alkylation may be simply described as the addition or insertion of an alkyl group into a substrate molecule. Of particular interest is the alkylation of aromatic and hydroxy aromatic substrates, such as benzene, toluene, xylene and phenol. Suitable alkylating agents include, for example, olefins, alkanes, alkyl halides and mixtures. However, particularly preferred alkylating agents for use in the present invention include olefins, including olefin oligomers, such as propylene oligomers, having from about 6 to about 50 carbon atoms and having one double bond per molecule.

A significant advantage of the present catalyst systems is that they are stable, i.e., the Lewis acids are immobilized and substantially retained on the substrate; i.e., do not leach or otherwise deposit free Lewis acid into the reaction medium or, more importantly, into the reaction products. Another advantage is that the present catalyst systems are usable for multiple hydrocarbon conversion cycles, e.g., polymerization or alkylation cycles (in the context of a batch process) without regeneration, resulting in substantial cost savings, as well as the elimination of significant amounts of hazardous waste typically generated in conventional Lewis acid processes. Not only can the supported Lewis acid catalyst systems of the present invention be employed for multiple reaction cycles, or on a continuous basis for extended times of reaction (e.g., polymerization, alkylation, isomerization or cracking), but they can also be recovered readily by simple filtration techniques.

DETAILED DESCRIPTION OF THE PREFERRED EMBODIMENTS

The novel immobilized Lewis acid catalyst systems of the present invention may be prepared by fixing or immobilizing at least one Lewis acid on the surface of an inorganic substrate which contains surface —OH groups.

For the purposes of this invention, the terms fixed or immobilized are used interchangeably and are defined as wherein substantially all of the active Lewis acid(s) is chemically bound to the substrate, e.g., by forming oxygen-metal bonds with the metal(s) of the Lewis acid. In other words, the Lewis acid is not readily extracted from the substrate by a solvent, diluent or reactant under conditions of use; during, e.g., polymerization, alkylation, isomerization or cracking.

The process for preparing the immobilized Lewis acid catalyst system of this invention comprises the steps of:

(a) providing an inorganic, hydroxyl group-containing support; and (b) contacting the support under conditions effective to react a portion of the hydroxyl groups contained on the support, with at least one compound having the formula $X_nMR_m$, wherein R is a monovalent hydrocarbon radical; X is selected from the group of halides consisting of Cl, Br and F; M is a metal selected from the group consisting of aluminum, boron gallium, antimony, tantalum, niobium, yttrium, cobalt, nickel, iron, tin, zinc, magnesium barium strontium, calcium, tungsten, molybdenum and the metals of the lanthanide series of Group 3 of the Periodic table of the elements (including lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb) and lutetium (Lu)); and n and m are integers sufficient to satisfy the valence requirements of M, thereby generating —O—M containing groups; and (c) contacting the reacted support of step (b) with at least one strong Bronsted acid, wherein the strong Bronsted acid is selected from the group consisting of acids equal to or stronger than 100% sulfuric acid, including mineral and organic acids, and having a Hammett acidity value of at least minus 12 or lower, preferably minus 13 or lower, under conditions effective to react the strong Lewis acid with the —O—M containing groups on the support. Use of more than one compound of the formula $X_nMR_m$ and/or more than one strong Bronsted acid provides an opportunity to produce an immobilized catalyst comprising more than one Lewis acid.

The general chemical reaction of the invention is represented schematically as follows:

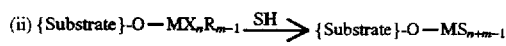

where SH is a strong Bronsted acid, as referred to above and further defined hereinafter.

Substrates useful in the present invention, to which the resulting Lewis acids are fixed, include any of the conventional inorganic oxide substrates which contain free hydroxyl groups which can react with the alkyl metal halide intermediate, $X_nMR_m$. Generally speaking, any metal oxide which has surface hydroxyl groups can be utilized as the substrate. The terms "metal oxide" and "inorganic oxide", although typically used herein in the singular, are meant to include both single oxides, such as silica or alumina, as well plural and complex oxides, such as silica-alumina, silica-alumina-thoria, zeolites and clays.

Non-limiting examples of such inorganic oxides include silica, alumina, titania, magnesia, silica-alumina, silica-titania, silica-magnesia, silica-alumina-thoria, silica-alumina-zirconia, crystalline aluminosilicates, including synthetic zeolites such as, for example, A, X, and ZSM-5 zeolites, and naturally occurring zeolites such as, for example, faujasite and mordenite, and open lattice clays, such as bentonite and montmorillonite. The preferred inorganic oxide substrates typically are in the form of powders or particles, and include a major component of silica or alumina or a mixture of both.

Particularly suitable as substrates are those solid inorganic oxide compositions known as metal oxide gels or gel oxides. Preferred oxide gel materials include those gel materials selected from the group consisting of silica, alumina, alumina-silica, zeolites and open lattice clays. Silica gel and silica-alumina gel substrates are particularly preferred.

The particular substrate materials are not critical, provided that they do not interfere with the reaction processes for which the resulting immobilized Lewis acid catalyst systems are intended to be used, and provided that they contain the hydroxyl groups which are necessary to react with the alkyl metal halide, and thereby fix or immobilize, the Lewis acid catalyst materials.

The compound of the formula $X_nMR_m$, wherein R is a monovalent hydrocarbon radical, X is selected from the group of halides consisting of Cl, Br and F; M is a metal selected from the group consisting of aluminum, boron, gallium, antimony, tantalum, niobium, yttrium, cobalt, nickel, iron, tin, zinc, magnesium barium strontium, calcium, tungsten, molybdenum and the metals of the lanthanide series, and n and m are integers sufficient to satisfy the valence requirements of M, is used in order to react with the OH groups of the substrate, thereby generating —O—M— containing groups for further reaction with the strong Bronsted acid, as described above. If n is equal to zero, the compound is a metal alkyl and if m is equal to zero the compound is a metal halide (for convenience, the compound is referred to generically as an alkyl metal halide). Each of these compounds can be used so long as the overall reaction can be achieved in view of the particular metal selected and the particular substrate of interest. Useful compounds include $AlCl_3$, $C_2H_5AlCl_2$, $(C_2H_5)_2AlCl$, $(C_2H_5)_3Al$ as well as $BCl_3$, $SnCl_4$, and $MgBu_2$. Such alkyl metal halides are themselves considered to be Lewis acids of varying strengths, but as used in the instant invention, these compounds serve an intermediate function as described above.

Alkyl metal halides which are regarded as strong or weak Lewis acids in their own right are useful in the instant invention as described above. Among those considered to be strong Lewis acids are the halides, alkyl halides and alkyl compounds of aluminum and the halides of boron, and equivalents thereof. Preferred are compounds where R is a monovalent hydrocarbon radical, preferably $C_1$–$C_{12}$ alkyl or aryl. Non-limiting examples of such strong Lewis acids include triethyl aluminum, $(C_2H_5)_3Al$, diethyl aluminum chloride, $(C_2H_5)_2AlCl$, ethyl aluminum dichloride, $(C_2H_5)AlCl_2$, ethyl aluminum sesquichloride, $(C_2H_5)_{1.5}AlCl_{1.5}$, aluminum chloride, $AlCl_3$, and mixtures thereof. Among those considered to be relatively weak alkyl metal halide Lewis acids contemplated for use in this invention are the halides, alkyl halides and alkyl compounds of magnesium, and equivalents thereof, including, for example, magnesium compounds including dibutyl magnesium $((C_4H_9)_2Mg)$ and butyl magnesium chloride $(C_4H_9MgCl)$. Similarly, the other metals recited above can also be used in the alkyl metal halide.

The catalyst immobilization reaction can be carried out by contacting the inorganic substrate with at least one metal alkyl halide at a temperature ranging from somewhat below room temperature to elevated temperatures on the order of about 150° to 200° C. or higher, and preferably, from about room temperature, 20° C., to about 110° C. The second step of the process is more conveniently conducted at a somewhat lower temperature, for example, from about −80° to about 100° C.; preferably from about −60° to about 70° C.; more preferably from about −50° to about 50° C.

The concentration of total Lewis acid present on the substrate will range from about 0.5 to about 20% by weight, based on the total weight of Lewis acid metal; preferably from about 1 to about 10%; most preferably from about 2 to about 8%; for example, about 5 weight % of total Lewis acid metal on the substrate.

As used in this specification and claims, the term "strong Bronsted acid" is meant to define mineral acids stronger than hydrochloric acid and organic acids having a Hammett acidity value of at least minus 10 or lower, preferably at least minus 12 or lower, under the same conditions employed in context with the herein described invention. Among the preferred strong acids are 100% $H_2SO_4$ (sulfuric acid), $HClO_4$ (perchloric acid), $CF_3SO_3H$ (trifluoromethanesulfonic acid), $HSO_3F$ (fluorosulfonic acid), and $HSO_3Cl$ (chlorosulfonic acid) (as described in Chemtech, November 1993, pages 23–29, incorporated herein by reference. The subject of superacids and Bronsted-Lewis superacid mixtures and their relationship to Friedel-Crafts reactions is also treated in "Encyclopedia of Chemical Technology, third edition, Vol. 11, pages 295–296, incorporated herein by reference). The Hammett acidity function is defined as:

$$H_o = pK_{BH^+} - \log(BH^+/B)$$

where $pK_{BH^+}$ is the dissociation constant of the conjugate acid and $BH^+/B$ is the ionization ratio; lower negative values of Ho correspond to greater acid strength.

A specific example of the reaction sequence of the present invention is illustrated as follows:

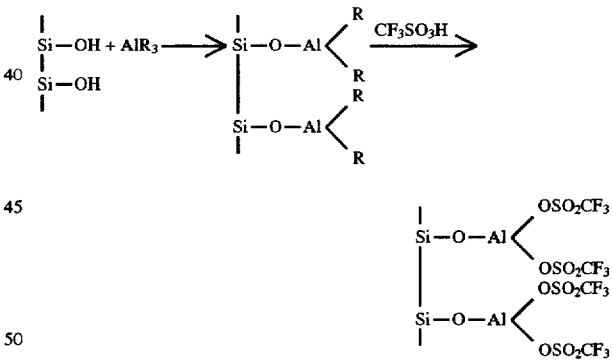

The novel immobilized catalysts of the present invention can be used to polymerize a variety of monomers into homopolymers and copolymers, e.g., polyalkenes. The monomers include those having unsaturation which are conventionally polymerizable using carbocationic Lewis acid catalyst polymerization techniques, and monomers which are the equivalents thereof. The terms cationic and carbocationic are used interchangeably herein. Olefin monomers useful in the practice of the present invention are polymerizable olefin monomers characterized by the presence of one or more ethylenically unsaturated groups. The monomers can be straight or branched monoolefinic monomers, such as vinyl ethers, propylene, 1-butene, isobutylene, and 1-octene, or cyclic or acyclic conjugated or non-conjugated dienes.

Suitable olefin monomers are preferably polymerizable terminal olefins: that is, olefins characterized by the presence in their structure of the group $>C=CH_2$. However, polymerizable internal olefin monomers (sometimes referred to in the patent literature as medial olefins) characterized by the presence within their structure of the group

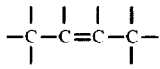

can also be used to form polymer products. When internal olefin monomers are employed, they normally will be employed with terminal olefins to produce polyalkenes which are interpolymers. For purposes of the invention, when a particular polymerized olefin monomer can be classified as both a terminal olefin and an internal olefin, it will be deemed to be a terminal olefin. Thus, 1,3-pentadiene (i.e., piperylene) is deemed to be a terminal olefin for purposes of this invention.

Preferred monomers used in the method for forming a polymer in accordance with the present invention are preferably selected from the group consisting of alpha-olefins and typically $C_3$-$C_{25}$ alpha olefins. Suitable alpha-olefins may be branched or straight chain, cyclic, and aromatic substituted or unsubstituted, and are preferably $C_3$-$C_{16}$ alpha-olefins. Mixed olefins can be used (e.g., mixed butenes).

The alpha-olefins, when substituted, may be directly aromatic substituted on the 2-carbon position (e.g., monomers such as $CH_2=CH-C_6H_5$ may be employed). Representative of such monomers include styrene, and derivatives such as alpha-methyl styrene, para-methyl styrene, vinyl toluene and its isomers.

In addition, substituted alpha-olefins include compounds of the formula $H_2C=CH-R^3-X^2$ wherein $R^3$ represents $C_1$ to $C_{22}$ alkyl, preferably $C_1$ to $C_{10}$ alkyl, and $X^2$ represents a substituent on $R^3$ and can be aryl, alkaryl, or cycloalkyl. Exemplary of such $X^2$ substituents are aryl of 6 to 10 carbon atoms (e.g., phenyl, naphthyl and the like), cycloalkyl of 3 to 12 carbon atoms (e.g., cyclopropyl, cyclobutyl, cyclohexyl, cyclooctyl, cyclodecyl, cyclododecyl, and the like) and alkaryl of 7 to 15 carbon atoms (e.g., tolyl, xylyl, ethylphenyl, diethylphenyl, ethyinaphthyl, and the like). Also useful are bicyclic, substituted or unsubstituted olefins, such as indene and derivatives, and bridged alpha-olefins of which $C_1$-$C_9$ alkyl substituted norbornenes are preferred (e.g., 5-methyl-2-norbornene, 5-ethyl-2-norbornene, 5-(2'-ethylhexyl)-2-norbornene, and the like).

Illustrative non-limiting examples of preferred alpha-olefins are propylene, 1-butene, isobutene, 1-pentene, 1-hexene, 1-octene, and 1-dodecene.

Dienes suitable for purposes of this invention include straight chain, hydrocarbon diolefins or cycloalkenyl-substituted alkenes having about 6 to about 15 carbon atoms, including, for example, 1,4-hexadiene, 5-methyl-1,4-hexadiene, 1,3-cyclopentadiene, tetrahydroindene, dicyclopentadiene, 5-methylene-2-norbornene, 5-cyclohexylidene-2-norbornene, 5-vinyl-2-norbornene, allyl cyclohexene and vinyl cyclododecene.

Of the non-conjugated dienes typically used, the preferred dienes are dicylcopentadiene, methyl cyclopentadiene dimer, 1,4-hexadiene, 5 methylene-2-norbornene, and 5-ethylidene-2-norbornene. Particularly preferred diolefins are 5-ethylidene-2-norbornene and 1,4-hexadiene.

The polymers and copolymers which can be manufactured by the process of the present invention are those which can be manufactured by a carbocationic polymerization process and include but are not limited to polyalkenes, such as polyisobutene, poly(1-butene), polystyrene, isobutene styrene copolymers, and the like. The term copolymer as used herein is defined to mean a polymer comprising at least two different monomer units.

The carbocationic polymerization process of the present invention may be carried out in a polar or, preferably, non-polar gas or, preferably, liquid reaction medium as a continuous, semi-continuous or batch process. Suitable polar solvents which may be used as the polymerization reaction medium include, for example, methyl chloride, dichloromethane, ethyl chloride or nitromethane or the like, whereas suitable non-polar solvents include, for example, carbon tetrachloride, hexane, heptane, cyclohexane, benzene, toluene, and more generally the linear or branched, saturated or unsaturated hydrocarbon solvents which can be found in the stream of monomers obtained from various cracking processes. Generally however, the use of non-polar solvents is preferred.

The reactors which may be utilized in the practice of the present invention include conventional reactors and equivalents thereof such as batch reactors, stirred tank reactors, fluidized bed reactors, and continuous tank or tubular reactors and the like; the process may be continuous, batch or semi-continuous or combinations thereof.

In particular, the immobilized catalysts of the present invention are especially useful for manufacturing polyisobutene and poly(1-butene) from feedstreams containing butene monomers. It is especially preferred to use refinery feed streams containing $C_4$ monomers, commonly referred to as Raffinate I and Raffinate II.

The polymers and copolymers which are manufactured using the immobilized Lewis acid catalyst system of the present invention may be referred to as reactive polymers in the sense that they are characterized by having terminal or non-terminal vinylidene unsaturation in about 40% of their polymer chains. This differs from polymer products which have been prepared using conventional non-supported Lewis acid catalysts wherein a single Lewis acid, such as ethyl aluminum dichloride, is employed (typically less than 20% of the chains of polymers of this type contain vinylidene unsaturation); in polymer products prepared using conventional $BF_3$ catalysts typically 40% or more of the polymer chains contain terminal vinylidene unsaturation.

For purposes of this comparison, polyisobutylene polymer chains having terminal vinylidene unsaturation may be illustrated as follows:

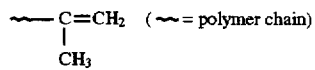

Polyisobutylene polymer chains having non-terminal (internal) vinylidene unsaturation may be illustrated as follows:

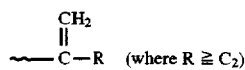

The reactor will contain sufficient amounts of the immobilized catalyst system of the present invention effective to catalyze the polymerization of the monomer containing feedstream such that a sufficient amount of polymer having desired characteristics is produced. The reaction conditions will be such that sufficient temperature, pressure and residence time are maintained effective to maintain the reaction medium in the liquid state and to produce the desired polymers having the desired characteristics.

Typically, the catalyst to monomer ratio utilized will be those conventional in this art for carbocationic polymerization processes. For example, catalyst to monomer mole ratios will typically be about 1/15000 to about 1/50, more typically about 1/5000 to about 1/100, and preferably about 1/1000 to about 1/200. This mole ratio will be calculated by determining the number of Lewis acid catalyst sites in the immobilized Lewis acid catalyst. This can be done by using conventional analytic testing techniques such as elemental analysis, NMR (e.g., aluminum NMR) and absorption spectroscopy. Once the number of Lewis acid sites per unit of immobilized catalyst is known, the mole ratio is calculated in a conventional manner.

The polymerization reaction temperature is conveniently selected based on the target polymer molecular weight and the monomer to be polymerized as well as standard process variable and economic considerations, e.g., rate, temperature control, etc. Typically temperatures from about $-100°$ C. to about $+75°$ C. are useful in the process; more typically about $-50°$ C. to about $+50°$ C., depending, as noted above, on polymer molecular weight. Reaction pressure will typically be about 200 kPA to about 1600 kPA, more typically about 300 to about 1200 kPA, and preferably about 400 to about 1000.

The monomer feedstream to this process may be at least one pure or mixed monomer feedstream or combinations thereof. Preferably, the monomer feedstream may be mixed with solvents such as hexane or heptane, and the like. A preferred feedstream to this process may be a pure or mixed refinery butene stream containing one or more of 1-butene, 2-butene, (cis and trans), and isobutene. The preferred feedstreams (preferred on an availability and economic basis) are available from refinery catalytic crackers and steam crackers. These processes are known in the art. The butene streams typically contain between about 6 wt. % to about 50 wt. % isobutylene together with 1-butene, cis- and trans-2-butene, isobutane and less than about 1 wt. % butadiene. One particularly preferred $C_4$ feedstream is derived from refinery catalytic or steam cracking processes and contains about 6–45 wt. % isobutylene, about 25–35 wt. % saturated butanes and about 15–50 wt. % 1- and 2-butenes. Another preferred $C_4$ feedstream is referred to as Raffinate II characterized by less than about 6 wt. % isobutylene.

The monomer feedstream is preferably substantially anhydrous, that is, it contains less than 50 ppm, and more preferably less than about 30 ppm, and most preferably less than about 10 ppm, by weight of water. Such low levels of water can be obtained by contacting the feedstream, prior to the reactor, with a water absorbent (such as NaH, $CaCl_2$, $CaSO_4$, molecular sieves and the like) or by the use of distillation drying.

The monomer feedstream is typically substantially free of any impurity which is adversely reactive with the catalyst under the polymerization conditions. For example, the monomer feed preferably should be substantially free of bases (such as caustic), sulfur-containing compounds (such as $H_2S$, COS, and organo-mercaptans, e.g., methyl mercaptan, ethyl mercaptan), N-containing compounds, and the like.

The monomer feedstream is typically substantially free of aromatic compounds to avoid alkylation reactions. Therefore, use of an aromatic solvent generally is not envisioned in this polymerization process.

A material acting as a cocatalyst (or promoter) may optionally be added, to a monomer feedstream before that feed is introduced to a reactor or it may be added separately to the reactor, e.g., to the catalyst bed. A variety of conventional cocatalysts or equivalents can be used including inorganic acids such as hydrogen halides, lower alcohols, $C_2$–$C_{24}$ secondary or tertiary alkyl halides, organic acids such as carboxylic acids and sulfonic acids, and the like. For example, gaseous, anhydrous HCl, may be employed as a cocatalyst. The HCl will be employed in a catalytically effective amount, which amount will generally range from about 50 to 5,000 ppm by weight of the monomer feed, preferably 50 to 500 ppm (e.g., 70 to 200 ppm) by weight of the monomer feed when the monomer feed comprises >5 wt. % isobutylene, and preferably from about 100–5,000 ppm (e.g., 400–3,000 ppm) by weight when the feed comprises n-butenes and <5 wt. % isobutylene. If anhydrous HCl is added to the feedstream containing isobutene, t-butyl chloride is formed before contact with the solid catalyst.

The order of contacting the monomer feedstream, catalyst, cocatalyst (if any), and solvent is not critical to this invention. Accordingly, the catalyst and cocatalyst can be added to the reactor before or after adding the monomer feedstream and solvent. Alternatively, the catalyst and monomer feedstream can be added before or after adding the cocatalyst and solvent.

The degree of polymerization of polymers (and oligomers) produced with the catalyst of this invention will be determined by the desired end use. Typically the degree of polymerization is from about 5 to 5,000; more typically from about 10 to about 1,000; for lower molecular weight polymers and oligomers the degree of polymerization will typically be about 5 to about 100. Correspondingly, the number average molecular weight, $M_n$, of a polymeric product will be determined by the monomer and degree of polymerization; for a $C_4$-based polymer typical values are from about 300 to about 300,000 gm/mole, depending on the intended end use of the product. Number average molecular weight is conveniently measured by a suitably calibrated gel permeation chromatography (GPC) instrument. The polydispersity index (PDI) of the polymer, also known as the molecular weight distribution ($M_w/M_n$), will typically range from about 4 to about 25, more typically about 5 to about 22, and preferably about 6 to about 20.

Lewis acid catalysts of the present invention also find use in other hydrocarbon conversion processes including alkylation, isomerization and cracking. For example, the catalysts may be employed in the cracking of long chain hydrocarbons, e.g., heptane, butane, etc., to produce shorter chain products such as ethane, propane, butanes, etc. Additionally, the catalysts may be used to catalyze the isomerization of normal alkanes to their branched chain isomers.

The alkylation process of the present invention will be conducted by contacting the aromatic or hydroxy aromatic substrate and alkylating agent under reaction conditions, including mole ratio, temperature, time and catalyst ratio sufficient to alkylate the substrate. The hydroxy aromatic substrate compounds useful in the preparation of the alkylated materials of this invention include those compounds having the formula:

$$Ar\text{-}(OH)_x$$

wherein Ar represents

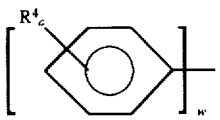

and z is an integer from 1 to 2, w is an integer from 1–3, a is 1 or 2 and $R^4$ is a $C_1$–$C_{24}$ alkyl radical. Illustrative of such Ar groups are phenylene, biphenylene, naphthalene and the like.

The aromatic substrate compounds useful in the preparation of the alkylated materials of this invention include those compounds having the formulas:

$$Ar^1\text{-}R^5_b \text{ and } (Ar^1\text{-}R^5_b)_y$$

wherein $Ar^1$ represents:

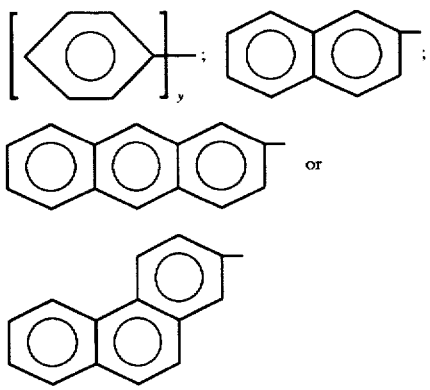

wherein b is one or two; $R^5$ is $C_1$–$C_{24}$ alkyl, $C_3$–$C_{24}$ cycloalkyl, $C_6$–$C_{18}$ aryl, $C_7$–$C_{30}$ alkylaryl, OH, or H; and y is 1–3. Illustrative of such $Ar^1$ groups are benzene, phenylene, biphenylene, naphthalene, and anthracene.

The substrate generally will be contacted in a molar ratio of from about 0.1 to 10 preferably from about 1 to 7, more preferably from about 2 to 5, moles of the substrate per mole of the alkylating agent. Conventional ratios of alkylating agent typically will be used. The ratio typically will be about 0.5 to 2:1, more typically about 0.8 to about 1.5:1, and preferably about 0.9 to about 1.2:1. The selected catalyst can be employed in widely varying concentrations. Generally, the catalyst will be charged to provide at least about 0.001, preferably from about 0.01 to 0.5, more preferably from about 0.1 to 0.3, moles of Lewis acid catalyst per mole of substrate charged to the alkylation reaction zone. Use of greater than 1 mole of the Lewis acid catalyst per mole of substrate is not generally required. The reactants can be contacted with the present immobilized Lewis acid catalyst system employing any conventional solid-liquid contacting techniques, such as by passing the reactants through a fixed bed of catalyst particles. The upper limit on the moles of catalyst employed per mole of substrate compound is not critical.

The temperature for alkylation can also vary widely, and will typically range from about 10° to 250° C., preferably from about 20° to 150° C., more preferably from about 25° to 80° C.

The alkylation reaction time can vary and will generally be from about 1 to 5 hours, although longer or shorter times can also be employed. The alkylation process can be practiced in a batchwise, continuous or semicontinuous manner.

Alkylation processes of the above types are known and are described, for example, in U.S. Pat. Nos. 3,539,633 and 3,649,229, the disclosures of which are hereby incorporated by reference.

Polybutenes and other polymers and copolymers in the molecular weight range of 500 to 10,000 prepared in accordance with the process of the present invention are particularly useful as a feedstream for the production of improved lubricating oil dispersants. These dispersants generally utilize a polybutene reaction product with a molecular weight, $M_n$, of 700 to 10,000, comprise the reaction product of polybutenyl succinic anhydride, or the acid form thereof, with monoamines or polyamines having at least one primary or secondary amino group such as the alkylene polyamines, particularly the ethylene polyamines, the polyoxyalkylene amines, aromatic and cycloaliphatic amines, hydroxyamines, monoaliphatic and dialiphatic substituted amines. Useful dispersants are also formed by reacting monohydric and polyhydric alcohols with the polyisobutenyl succinic anhydride or diacid provided in accordance with this invention and preferred materials are thus derived from polyols having 2 to 6 OH groups containing up to about 20 carbon atoms such as the alkene polyols and alkylene glycols. Also suitable are the polyoxyalkylene alcohols such as polyoxyethylene alcohols and polyoxypropylene alcohols, monohydric and polyhydric phenols and naphthols, ether alcohols and amino alcohols and the like. Borated derivatives of the foregoing dispersants are also useful, especially borated nitrogen containing dispersants resulting from boration with boron oxide, boron halide, boron acids and esters to provide 0.2 to 2.0 weight percent boron in the dispersant. Metals and metal-containing compounds can also form useful dispersants and these are compounds capable of forming salts with the polybutenyl succinic anhydride or acid (using the polybutenes of the present invention). These include metals such as the alkali metals, alkaline-earth metals, zinc, cadmium, lead, cobalt, nickel, copper, molybdenum, in the form of oxides, carboxylates, halides, phosphates, sulfates, carbonates, hydroxides and the like.

Lubricating oil compositions usually will contain dispersants in amounts of from about 1 to 15 weight percent based on the overall weight of the composition. Lubricating oil compositions typically will contain other additives in customary amounts to provide their normal attendant functions such as metal detergents or basic metal detergents, anti-wear additives, anti-oxidants, viscosity modifiers and the like. Dispersants are conventionally packaged and dispensed in the form of solution concentrates containing about 20 to 50 wt. % dispersant in a mineral oil.

The invention will be understood more fully in conjunction with the following examples which are merely illustrative of the principles and practice thereof. The invention is not intended to be limited by these illustrative examples. Parts and percentages where used are parts and percentages by weight, unless specifically noted otherwise.

EXAMPLE 1

Catalyst Synthesis

Silica (W. R. Grace 1952) having a specific area of 300 m²/g was dehydrated by heating under vacuum at 450° C. for one hour. To 2 g of the dehydrated silica in 50 ml of heptane, there was added 3 ml of a 1 molar solution of triisobutyl aluminum (TIBA) in heptane. After one hour at room temperature, the resulting solid was washed three times with heptane in order to remove unreacted TIBA.

There was then added to the solid, 50 ml of heptane, 0.4 ml of trifluoromethanesulfonic acid ($CF_3SO_3H$). After stirring for one hour at room temperature, the solid was washed twice with heptane and then dried under vacuum for one hour at 100° C.

EXAMPLE 2

Isobutene Polymerization

In a glass flask were introduced 0.14 g of catalyst prepared in accordance with the procedure described in example 1 and 100 ml of heptane. Starting at room temperature, isobutene was introduced in the reaction mixture by bubbling. The fast reaction increased the medium temperature to 30° C. The introduction of monomer was then stopped and the mixture allowed to stir for one hour. The liquid part of the mixture was then recovered by filtration on a paper filter. After evaporation of the solvent and unreacted monomer, 7 g of polymer with a number average molecular weight=350 g/mol and polydispersity index (PDI)=4 was recovered. Further analysis of the polymer by $^1$H-NMR showed the presence of 39.6 mole % vinylidene unsaturation.

EXAMPLE 3

Toluene Alkylation

To a glass flask is introduced 300 mg of catalyst prepared according to example 1, 50 ml of toluene and 10 ml of 1-hexene. After stirring for 5 hours at room temperature, the liquid part of the reaction mixture is recovered by filtration and analyzed by gas chromatography. The reaction mixture is constituted of unreacted 1-hexene, toluene, hexyltoluene, dihexyltoluene and trihexyltoluene.

What is claimed is:

1. A process for cationically polymerizing olefin monomers, which comprises contacting one or more olefin monomers olefin monomer under cationic polymerization reaction conditions with a catalytically effective amount of a supported Lewis acid catalyst system comprising an inorganic oxide substrate having immobilized thereon a catalytically effective amount of at least one strong Lewis acid comprising at least one metal salt of a strong Bronsted acid wherein said metal is selected from the group consisting of aluminum, boron gallium, antimony, tantalum, niobium, yttrium, cobalt, nickel, iron, tin, zinc, magnesium barium strontium, calcium, tungsten, molybdenum and the metals of the lanthamide series and wherein said strong Bronsted acid is selected from the group consisting of mineral and organic acids having a Hammett acidity value of minus 13 or lower.

2. The process according to claim 1, wherein said inorganic oxide substrate comprises a silica component.

3. The process according to claim 2, wherein said Bronsted acid is selected from the group consisting of $FSO_3H$, $HSO_3Cl$, $CF_3SO_3H$, and $HClO_4$.

4. A process for alkylating an aromatic or hydroxy aromatic substrate, which comprises contacting said substrate with an alkylating agent under alkylation conditions with a catalytically effective amount of a supported Lewis acid catalyst system comprising an inorganic oxide substrate having immobilized thereon a catalytically effective amount of at least one strong Lewis acid comprising at least one metal salt of a strong Bronsted acid wherein said metal is selected from the group consisting of aluminum, boron gallium, antimony, tantalum, niobium, yttrium, cobalt, nickel, iron, tin, zinc, magnesium barium strontium, calcium, tungsten, molybdenum and the metals of the lanthanide series and wherein said strong Bronsted acid is selected from the group consisting of mineral and organic acids having a Hammett acidity value of minus 13 or lower.

5. A process for preparing a supported Lewis acid catalyst system, which comprises the steps of:

(a) providing an inorganic, hydroxyl group-containing support; and (b) contacting said support under conditions effective to react a portion of said hydroxyl groups contained on said support, with at least one compound selected from the group consisting of compounds having the formula $X_nMR_m$, wherein R is a monovalent hydrocarbon radical; X is selected from the group of halides consisting of Cl, Br and F; M is selected from the group consisting of aluminum, boron gallium, antimony, tantalum, niobium, yttrium, cobalt, nickel, iron, tin, zinc, magnesium barium strontium, calcium, tungsten, molybdenum and the metals of the lanthanide series; and n and m are integers sufficient to satisfy the valence requirements of M, thereby generating —O—M containing groups; and (c) contacting said support of step (b) with at least one strong Bronsted acid, wherein said strong Bronsted acid is selected from the group consisting of mineral and organic acids having a Hammett acidity value of minus 13 or lower under conditions effective to react said strong Bronsted acid with the —O—M containing groups on said support.

6. In a hydrocarbon conversion process wherein at least one hydrocarbon is contacted with a conversion catalyst under conversion conditions, the improvement comprising contacting said hydrocarbon with the catalyst system of claim 1.

7. The process of claim 6 wherein said hydrocarbon conversion is isomerization.

8. The process of claim 6 wherein said hydrocarbon conversion is cracking.

* * * * *